(12) United States Patent
Bradley

(10) Patent No.: US 8,923,988 B2
(45) Date of Patent: Dec. 30, 2014

(54) METHOD FOR EPIDURAL STIMULATION OF NEURAL STRUCTURES

(71) Applicant: Boston Scientific Neuromodulation Corporation, Valencia, CA (US)

(72) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/026,586

(22) Filed: Sep. 13, 2013

(65) Prior Publication Data

US 2014/0088674 A1  Mar. 27, 2014

Related U.S. Application Data

(60) Provisional application No. 61/704,381, filed on Sep. 21, 2012.

(51) Int. Cl.
*A61N 1/00* (2006.01)
*A61N 1/05* (2006.01)

(52) U.S. Cl.
CPC .................................. *A61N 1/0553* (2013.01)
USPC ............................ 607/116; 607/39; 607/117

(58) Field of Classification Search
USPC ............................................ 607/39, 116–117
See application file for complete search history.

(56) References Cited

U.S. PATENT DOCUMENTS

2010/0094372 A1* 4/2010 Grill et al. ...................... 607/39

* cited by examiner

*Primary Examiner* — Nicole F Lavert
(74) *Attorney, Agent, or Firm* — Vista IP Law Group LLP

(57) ABSTRACT

A method for treating a patient having nociceptive pain in a body region using at least one electrode implanted within a spinal column of the patient. The method comprises conveying electrical stimulation energy from the at least one implanted electrode to an efferent motor neural structure innervating the body region, thereby inducing an endogenous chemical response within a spinal cord of the patient that treats the nociceptive pain. Another method for treating a patient suffering from a medical ailment. The other method comprises applying electrical stimulation energy to an efferent neural structure, thereby increasing the activation threshold of the efferent neural structure relative an afferent neural structure, and applying electrical stimulation energy to the afferent neural structure while the activation threshold of the efferent neural structure is increased, thereby modulating activity of the afferent neural structure to treat the medical ailment while minimizing stimulation of the efferent neural structure.

16 Claims, 12 Drawing Sheets

METHOD FOR EPIDURAL STIMULATION OF NEURAL STRUCTURES

RELATED APPLICATION DATA

The present application claims the benefit under 35 U.S.C. §119 to U.S. provisional patent application Ser. No. 61/704,381, filed Sep. 21, 2012. The foregoing application is hereby incorporated by reference into the present application in its entirety.

FIELD OF THE INVENTION

The present invention relates to tissue stimulation systems, and more particularly, to spinal cord stimulation (SCS) systems.

BACKGROUND OF THE INVENTION

Implantable neurostimulation systems have proven therapeutic in a wide variety of diseases and disorders. For example, SCS techniques, which stimulate the spinal cord tissue of the patient, have long been accepted as a therapeutic modality for the treatment of chronic neuropathic pain syndromes, and the application of (SCS) has expanded to include additional applications, such as angina pectoralis, peripheral vascular disease, and incontinence, among others. SCS is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via lead extension(s). The neurostimulation system may further include a handheld patient programmer to remotely instruct the neurostimulator to generate electrical stimulation pulses in accordance with selected neuromodulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation electrode(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

As discussed, SCS may be utilized to treat patients suffering from chronic neuropathic pain. To this end, mid- to high-frequency electrical stimulation is generally applied to the sensory afferents of the dorsal column (DC) nerve fibers at an amplitude that creates a relatively comfortable sensation of paresthesia. While the full mechanisms are pain relief are not well understood, it is believed that the perception of pain signals is inhibited via the gate control theory of pain, which suggests that enhanced activity of innocuous touch or pressure afferents via electrical stimulation creates interneuronal activity within the dorsal horn that releases inhibitory neurotransmitters (e.g., Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, stimulation electrodes are typically implanted within the dorsal epidural space to provide stimulation to the DC nerve fibers.

Although it would be desirable to epidurally stimulate DC nerve fibers, various sensitive neural structures, including the DR and ventral root (VR) nerve fibers, are in close proximity to DC nerve fibers. As a result, SCS stimulation to treat chronic neuropathic pain may be difficult to accomplish without also inadvertently creating side-effects, e.g., in the form of uncomfortable muscle contractions and pain resulting from the inadvertent activation of the VR nerve fibers, either by reflex (via DR stimulation) or by direct VR stimulation, or both. There, thus, remains a need to minimize activation of efferent neural structures, while stimulating or at least modulating afferent neural structures.

Alongside the neuropathic pain (typically well-treated by SCS), patients may also experience nociceptive pain, resulting from nerve impingement or inflammation. In such instances, the nociceptive pain is rarely useful for protection or survival and thus could be dispensed with. Opioids are often used to manage nociceptive pain, but they can have significant side effects when taken chronically and systemically. Interventional procedures using ablation can be effective, but are necessarily destructive and may have undesirable sequelae. Other interventions using local steroids or anesthetics can be very effective, but require accurate needle placement by a physician. Acupuncture is another method for treating nociceptive pain as is low frequency/high intensity Transcutaneous Electrical Nerve Stimulation (TENS). Both of these treatments engender an endogenous opioid release ostensibly by mild activation of low threshold pain afferents (A-delta nerve fibers). Acupuncture typically requires a specialist for needle placement and can be inconvenient. Low frequency/high intensity TENS can also be inconvenient, requiring skin patch applications. There, thus, remains a need for a convenient stimulation procedure that would ameliorate nociceptive pain.

SUMMARY OF THE INVENTION

In accordance with one aspect of the present inventions, a method for treating a patient having nociceptive pain in a body region using at least one electrode implanted within a spinal column of the patient (e.g., in an epidural space, and preferably in the anterior epidural space, of the patient) is provided. If the body region is, e.g., the lower back, the electrode(s) may be implanted within a T7-T10 vertebral level of the spinal column. The method comprises conveying electrical stimulation energy from the implanted electrode(s) to an efferent motor neural structure (e.g., a ventral root (VR) fiber) innervating the body region, thereby inducing an endogenous chemical response (e.g., monoaminergic or opioidergic) response within a spinal cord of the patient that treats the nociceptive pain. The electrical energy may be conveyed from the implanted electrode(s) for at least 5 minutes per day when the patient is at rest.

In one optional method, the patient also has neuropathic pain in the body region, and at least another electrode is implanted within the spinal column of the patient. In this case, the method may further comprise conveying electrical stimulation energy from the other implanted electrode(s) to an afferent neural structure innervating the body region, thereby inducing an endogenous neurotransmitter inhibitory response within a spinal cord of the patient that treats the neuropathic pain. The electrical stimulation energy conveyed from the first implanted electrode(s) may have a relatively low frequency (e.g., in the range of 0.1-15 Hz) and a relatively low amplitude, while the electrical energy conveyed from the other implanted electrode(s) may have a relatively high frequency (e.g., greater than 50 Hz) and a relatively low amplitude.

In accordance with another aspect of the present inventions, a method for treating a patient suffering from a medical ailment (e.g., chronic pain) is provided. The method comprises applying electrical stimulation energy to an efferent neural structure (e.g., a ventral root (VR) fiber), thereby increasing the activation threshold of the efferent neural structure relative an afferent neural structure (e.g., a dorsal root (DR) fiber, or one of a dorso-spinal column fiber, dorso-lateral spinal column fiber, and a ventro-lateral spinal column fiber), and applying electrical stimulation energy to the afferent neural structure while the activation threshold of the efferent neural structure is increased, thereby modulating activity of the afferent neural structure to treat the medical ailment while minimizing, and preferably preventing, stimulation of the efferent neural structure. In one method, the electrical stimulation energy is epidurally applied to the afferent neural structure and the efferent neural structure.

The activation threshold of the efferent neural structure relative to the activation threshold of the afferent neural structure may be increased by applying electrical suppression energy to the efferent neural structure. For example, the electrical stimulation energy may be applied to afferent neural structure by sinking electrical current into at least one electrode adjacent the afferent neural structure, thereby treating the medical ailment, and the electrical suppression energy can be applied to the efferent neural structure by sourcing at least a portion of the electrical current from at least another electrode adjacent the efferent neural structure, thereby increasing the activation threshold of the efferent neural structure. At least a portion of the electrical current sourced at the other electrode(s) may be sunk into a remote electrode.

The activation threshold of the efferent neural structure may alternatively be increased by applying a sub-threshold, disabling conditioning pre-pulse (e.g., one having a duration less than 2000 µs) to the efferent neural structure, and the electrical stimulation energy may be applied to the afferent neural structure by applying a depolarizing stimulation pulse to the afferent neural structure.

The activation threshold of the efferent neural structure may alternatively be increased by applying electrical background energy to the efferent neural structure in accordance with at least one stochastic parameter. In one method, the stochastic parameter(s) comprises at least one of an interpulse interval, pulse amplitude, pulse shape, and pulse duration. In another method, the electrical background energy may comprise white noise, in which case, the stochastic parameter may comprise a frequency.

An optional method further comprises sensing neural activity in the efferent neural structure in response to the application of electrical stimulation energy to the afferent neural structure, in which case, the electrical stimulation energy may be applied to the efferent neural structure in response to sensing of the neural activity in the efferent neural structure.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
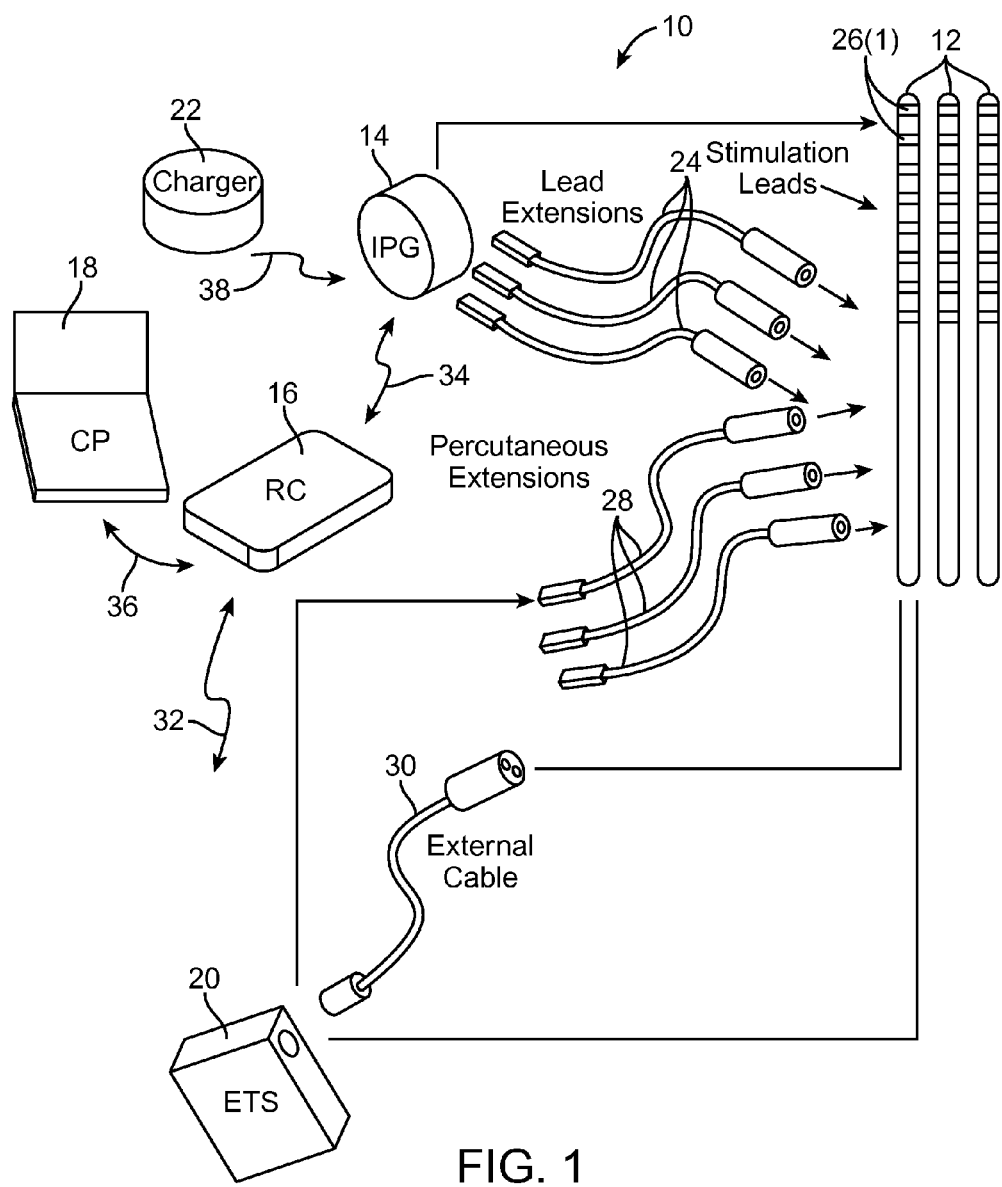
FIG. 1 is a plan view of a Spinal Cord Stimulation (SCS) system constructed in accordance with one embodiment of the present inventions.

Turning first to FIG. 1, an exemplary SCS system 10 generally comprises a plurality of neuromodulation leads 12 (in this case, three), an implantable pulse generator (IPG) 14 (or alternatively RF receiver-stimulator), an external remote control (RC) 16, a Clinician's Programmer (CP) 18, an External Trial Stimulator (ETS) 20, and an external charger 22.

The IPG 14 is physically connected via one or more lead extensions 24 to the neuromodulation leads 12, which carry a plurality of electrodes 26 arranged in an array. The neuromodulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of neuromodulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 in accordance with a set of neuromodulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different neuromodulation parameter sets. The IPG 14 may also be operated to modify the programmed neuromodulation parameters to actively control the characteristics of the electrical stimulation energy output by the IPG 14. As will be described in further detail below, the CP 18 provides clinician detailed neuromodulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The detailed neuromodulation parameters provided by the CP 18 are also used to program the RC 16, so that the neuromodulation parameters can be subsequently modified by operation of the RC 16 in a stand-alone mode (i.e., without the assistance of the CP 18). The charger 22 may also communicate with the IPG 14 via a communications link 38.

Figure 2:
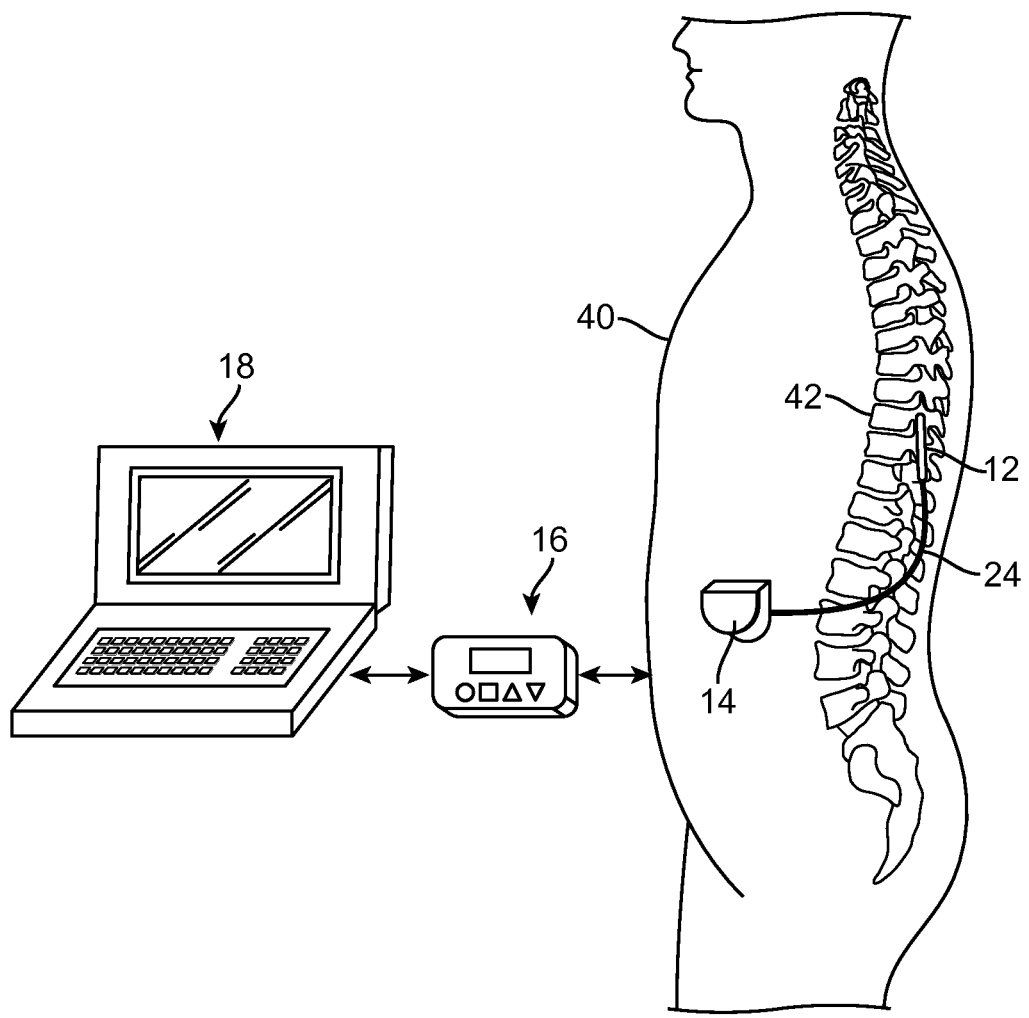
FIG. 2 is a plan view of the SCS system of FIG. 1 in use within a patient.

As shown in FIG. 2, the neuromodulation leads 12 are implanted within the spinal column 42 of a patient 40. The preferred placement of the electrode leads 12 is adjacent, and preferably in the epidural space above, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
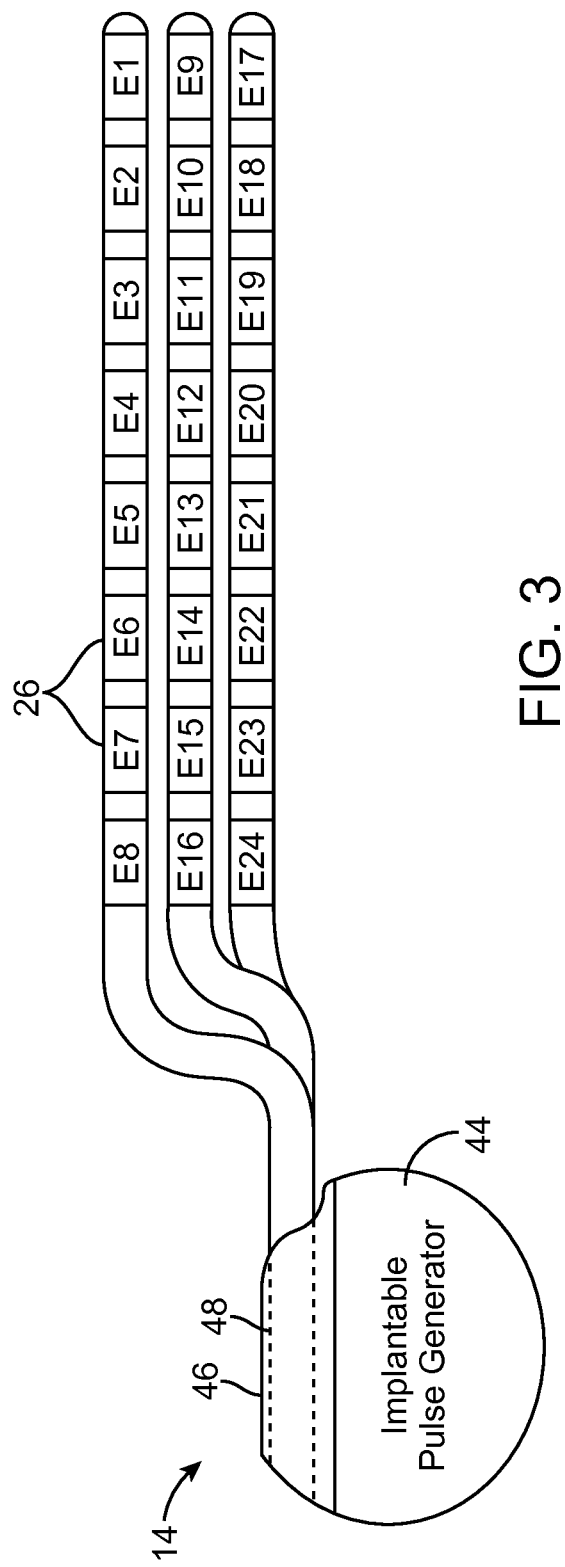
FIG. 3 is a plan view of an implantable pulse generator (IPG) and three percutaneous stimulation leads used in the SCS system of FIG. 1.

Referring now to FIG. 3, the external features of the neuromodulation leads 12 and the IPG 14 will be briefly described. Each of the neuromodulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
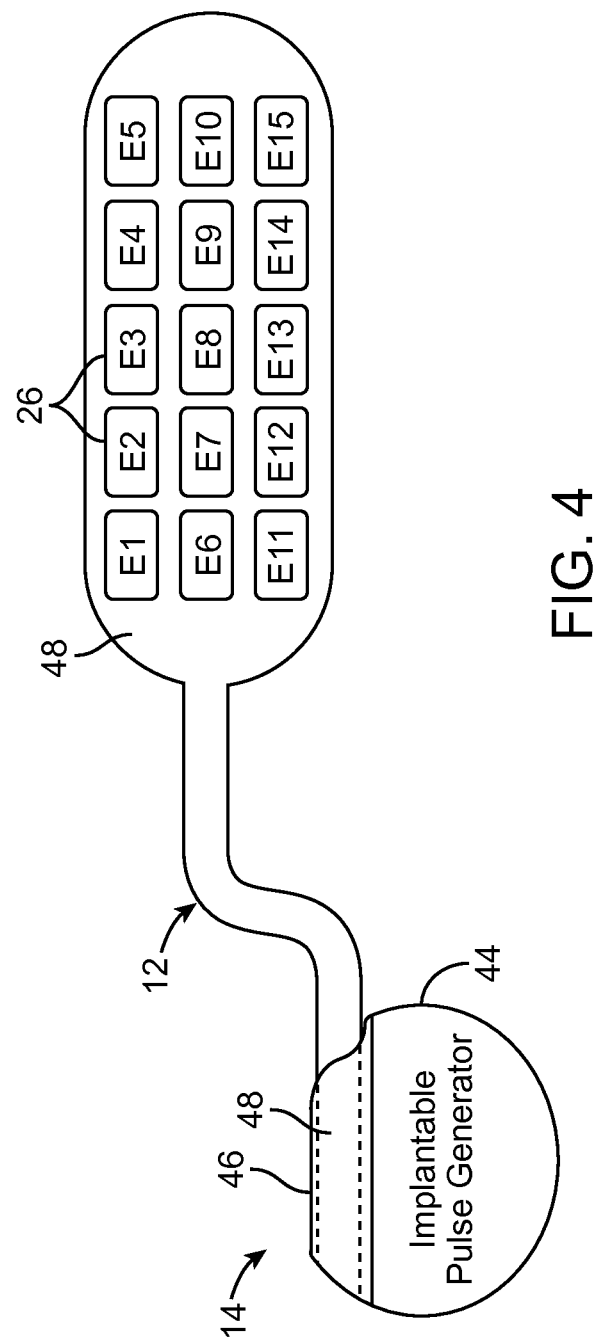
FIG. 4 is a plan view of an implantable pulse generator (IPG) and a surgical paddle lead used in the SCS system of FIG. 1.

Alternatively, as illustrated in FIG. 4, the neuromodulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the neuromodulation lead(s) 12. In the case where the lead extensions 24 are used, the port(s) 48 may instead receive the proximal ends of such lead extensions 24.

The IPG 14 includes pulse generation circuitry that provides electrical neuromodulation (conditioning and/or stimulation) energy in the form of a pulsed electrical waveform to the electrode array 26 in accordance with a set of neuromodulation parameters programmed into the IPG 14. Such neuromodulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Neuromodulation energy may be conveyed between two (or more) activated electrodes, one of which may be the IPG case 44. Neuromodulation energy may be transmitted to the tissue in a monopolar or multipolar (e.g., bipolar, tripolar, etc.) fashion. Monopolar neuromodulation occurs when a selected one of the lead electrodes 26 is activated along with the case 44 of the IPG 14, so that neuromodulation energy is transmitted between the selected electrode 26 and the case 44. Bipolar neuromodulation occurs when two of the lead electrodes 26 are activated as anode and cathode, so that neuromodulation energy is transmitted between the selected electrodes 26. For example, an electrode on one lead 12 may be activated as an anode at the same time that an electrode on the same lead or another lead 12 is activated as a cathode. Tripolar neuromodulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The neuromodulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) neuromodulation pulse and an anodic (positive) recharge pulse that is generated after the neuromodulation pulse to prevent direct current charge transfer through the tissue, thereby avoiding electrode degradation and cell trauma. That is, charge is conveyed through the electrode-tissue interface via current at an electrode during a neuromodulation period (the length of the neuromodulation pulse), and then pulled back off the electrode-tissue interface via an oppositely polarized current at the same electrode during a recharge period (the length of the recharge pulse).

Figure 5:
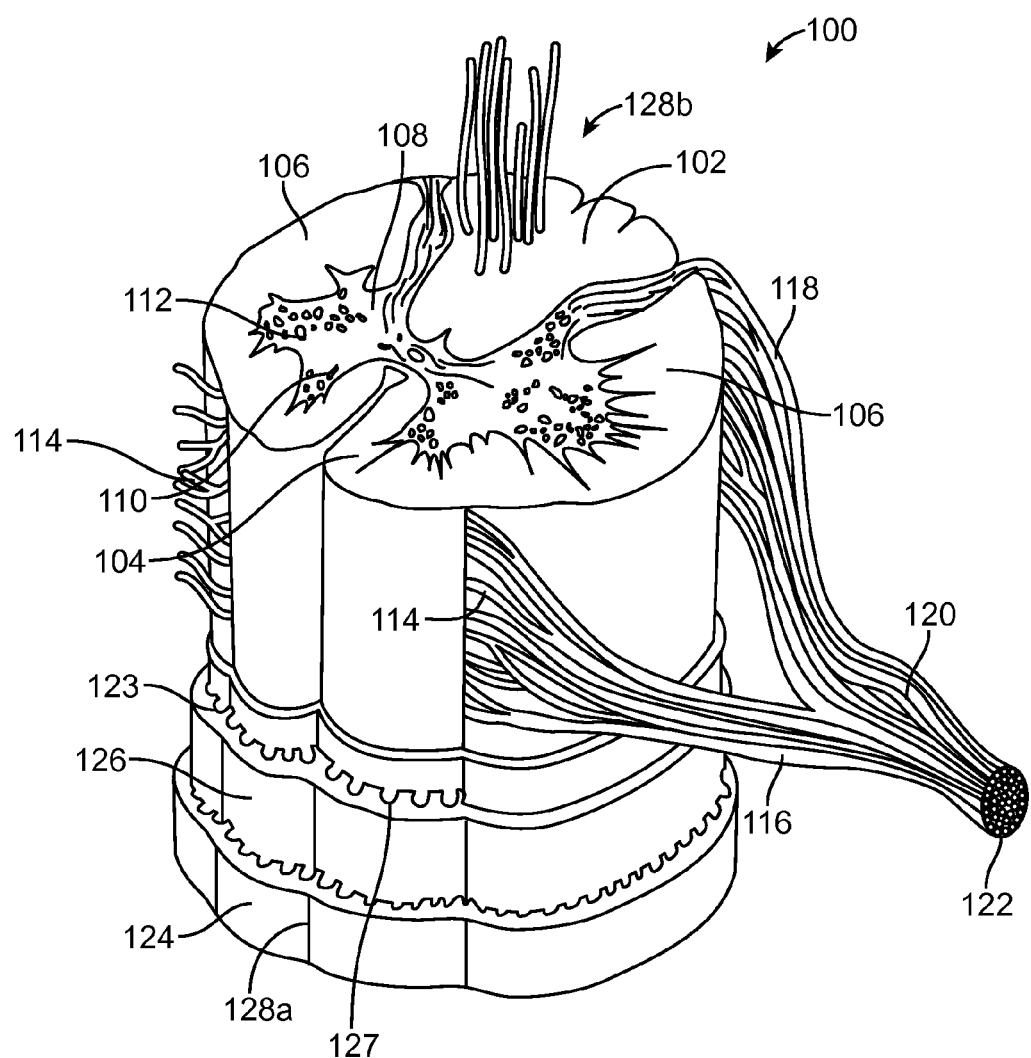
FIG. 5 is a pictorial view of the spinal cord and spinal nerves.
Figure 6:
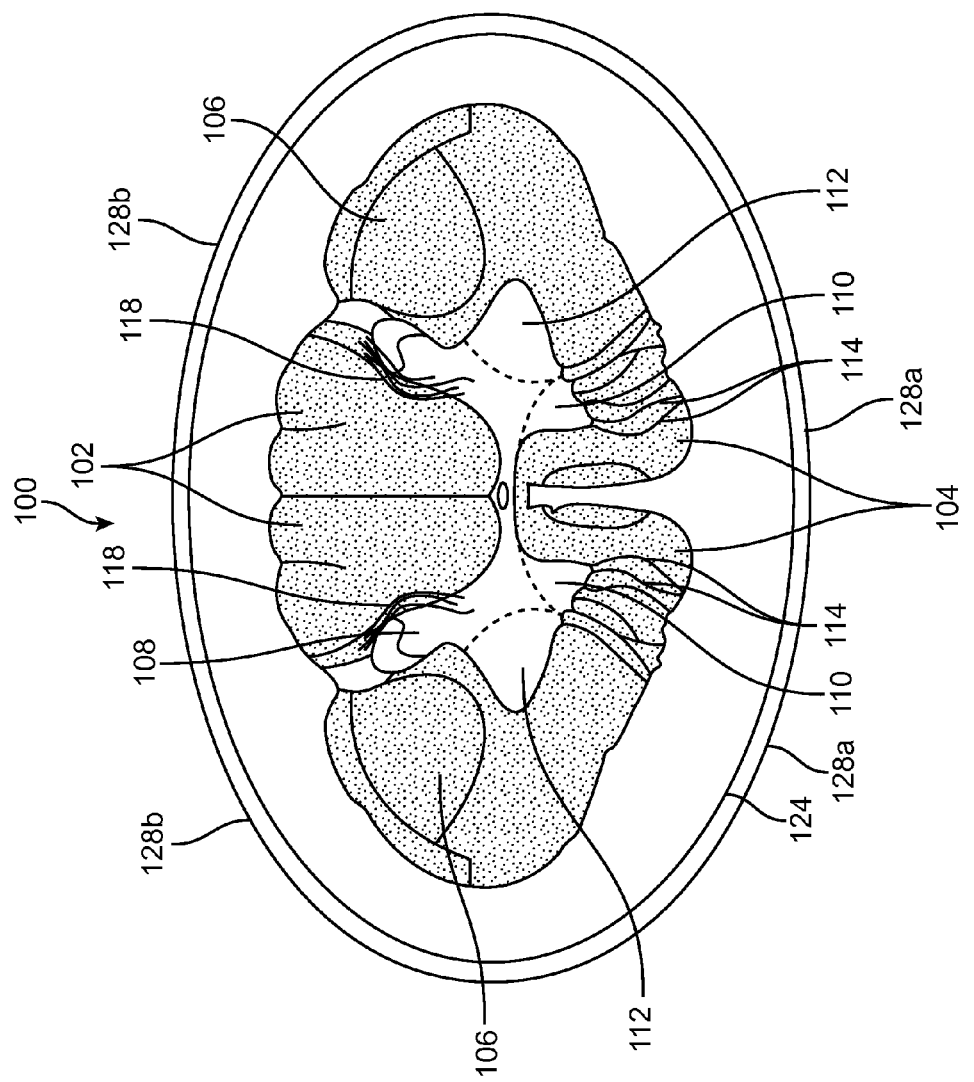
FIG. 6 is a cross-sectional view of the spinal cord.

Referring now to FIGS. 5 and 6, the portions of the spinal cord 100 that are relevant to the present inventions will be described. The spinal cord 100 is divided into three columns: the dorsal column 102, the ventral column 104, and the lateral columns 106. Similarly, the butterfly-shaped gray matter of the spinal cord 100 is divided into the dorsal horn 108, the ventral horn 110, and the lateral horn 112. A ventral median fissure 109 divides the spinal cord 100 into two lateral halves.

A group of motor nerve rootlets (ventral root nerve fibers) 114 branch off of the ventral horn 110 and combine to form the ventral root (VR) 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

The spinal cord 100 is protected by three layers of connective tissue, the dura mater 124, the arachnoid 126, and the pia mater 123, collectively referred to as meninges. An epidural space 128 surrounds the dura mater 124, and a subararchnoid space 130 lies under the arachnoid 126. The epidural space 128 may be topologically divided into two halves: a ventral epidural space 128*a* and a dorsal epidural space 128*b*.

Having described the structure and function of the SCS system 10, various techniques in using the SCS system 10 treat chronic pain will now be described. In each of these techniques, one or more of the percutaneous leads and/or the surgical paddle lead 12 illustrated in FIGS. 3 and 4 may be implanted within the epidural space 128. For purposes of simplicity and brevity, the techniques described below use the minimum number of electrodes (in some cases, only one electrode, and in other cases, two electrodes), although additional electrodes may be used. In conventional SCS techniques, stimulation is applied to the dorsal column 102 of the spinal cord 100 to treat chronic neuropathic pain, and accordingly, stimulation electrodes are positioned in the dorsal epidural space 128*b*.

Figure 7:
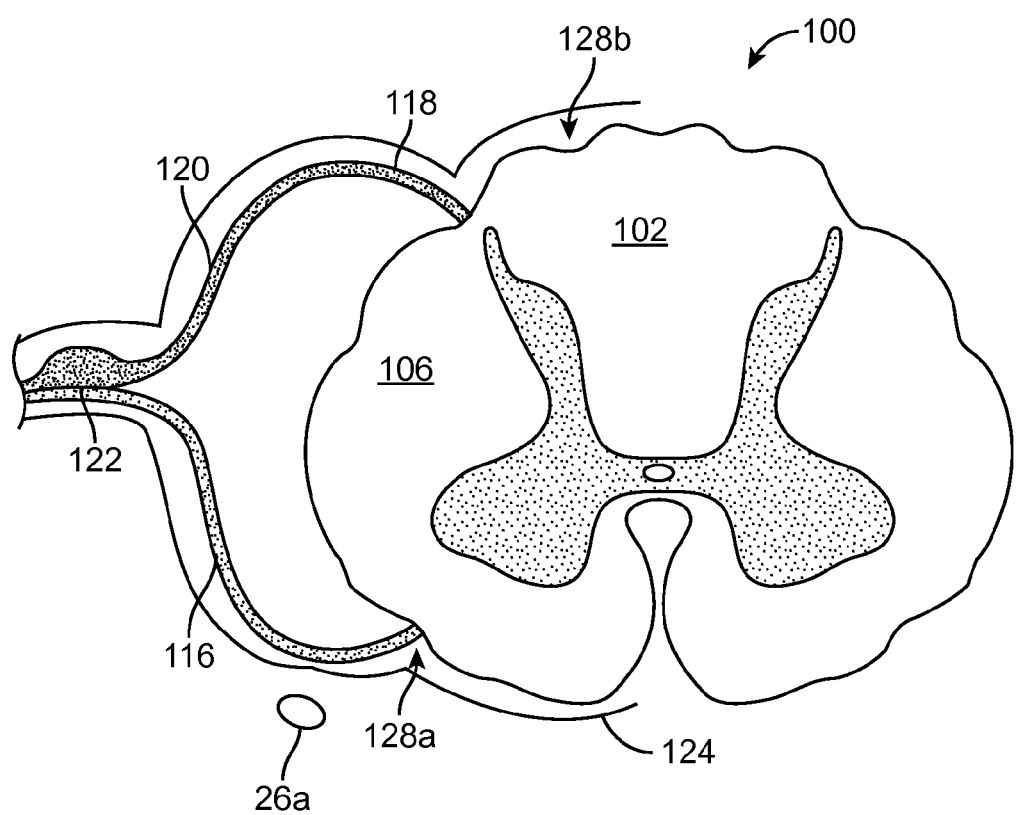
FIG. 7 is a perspective view showing a single-electrode arrangement relative to the spinal cord and spinal nerves in accordance with a first stimulation regimen of the present invention.

In contrast to conventional SCS techniques, which stimulate the dorsal column 102 of the spinal cord 100 to treat neuropathic pain, a technique used by the SCS system 10 to treat nociceptive pain experienced by the patient in a particular body region will now be described with reference to FIG. 7. The location of the electrode placement and stimulation regimen associated with this technique mildly stimulates efferent neural structures, such as, for example, motor nerve rootlets 114 and the ventral root 116, thereby engendering an endogenous chemical response designed to treat the nociceptive pain experienced by the patient. For example, the chemical response may be an opioidergic response or a monoaminergic (e.g., one that releases dopamine, serotonin, and/or norepinephrine).

To this end, a ventral electrode 26*a* may be implanted within the ventral epidural space 128*a* proximal to the ventral root 116. The vertebral level of the spinal column in which the electrode 26*a* is implanted will depend on the region in which the pain is perceived. For example, for low back pain, optimal locations are generally in or near the T7-T10 vertebral levels.

In the illustrated embodiment, stimulation is delivered at a relatively low rate (e.g., 0.1-15 Hz) with a relatively brief pulse width (e.g., 20-200 μs), and a relatively low amplitude at a level creating a mild, but clear, motor sensation (i.e., just high enough to engender just-tolerable motor activity in or near the region of pain). Stimulation times can be varied and can be programmed for delivery in bursts, such as 10 pulses on/20 pulses off, or the stimulation can be continuously applied for a set period of time, such as 5-20 minutes to engender a long-lasting neurotransmitter release over the period following the stimulation. Best results have been observed when the patient is still and resting.

Figure 8:
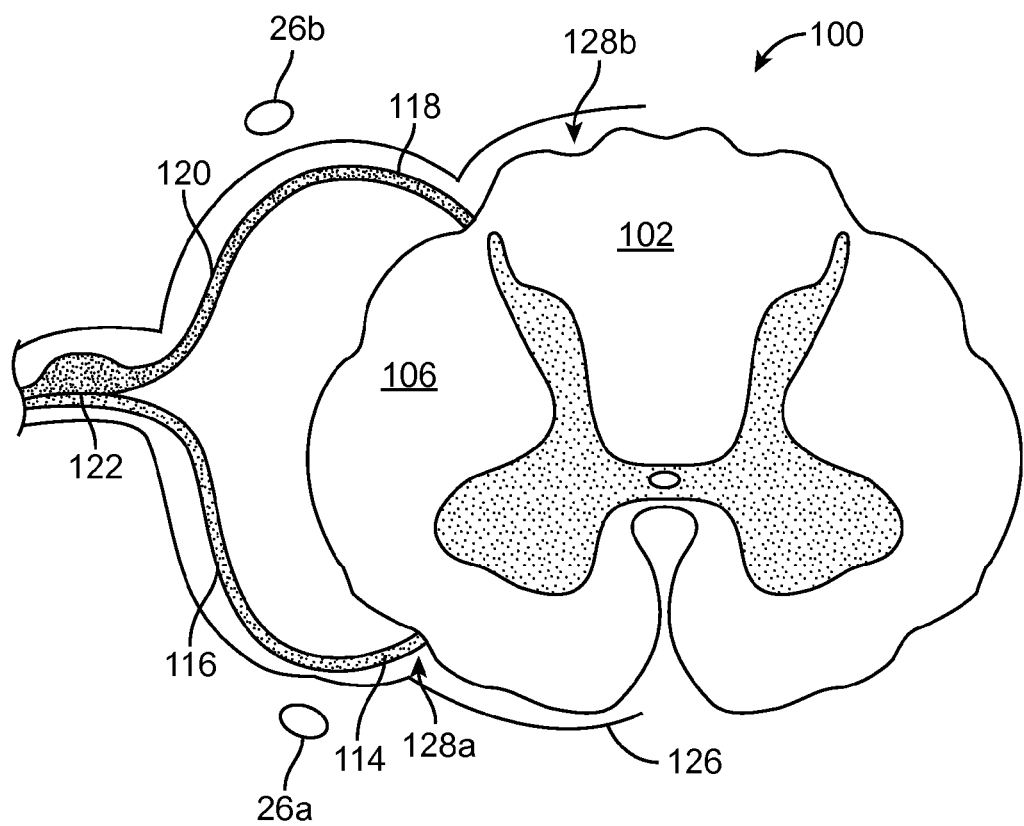
FIG. 8 is a perspective view showing a double-electrode arrangement relative to the spinal cord and spinal nerves in accordance with a first stimulation regimen of the present invention.

Referring to FIG. 8, an optional technique for treating both neuropathic pain and nociceptive pain will now be described. As in the embodiment of FIG. 7, a ventral electrode 26*a* is located near the ventral root 116. In addition, a dorsal electrode 26*b* is located in the dorsal epidural space 128*b* near sensory nerve rootlets 118 and dorsal root 120. In this technique, electrical energy can be supplied to the ventral electrode 26*a* in accordance with the stimulation parameters discussed in connection with FIG. 7.

The dorsal electrode 26*b*, however, can also be employed to provide motor stimulation by activating the dorsal root 120 through reflex facilitation. This stimulation regimen for the dorsal electrode 26*b* can employ similar stimulation parameters to those set out for the ventral electrode 26*a*, though at a lower amplitude. In this case, the two electrodes 26*a*, 26*b* could be programmed and energized separately, or they can interact, sharing current between them.

Alternatively, a high frequency/low intensity stimulation regimen can be employed for the dorsal electrode 26*b*. For example, the stimulation may be delivered at a relatively high rate (e.g., greater than 50 Hz). This stimulation regimen may engender local release of one or more inhibitory neurotransmitters within the dorsal horn 108 of the spinal cord 100, which would have the effect of ameliorating at least the neuropathic components of the patient's pain. In some circumstances at least some of the nociceptive pain might also be treated. Typical inhibitory neurotransmitters released by the stimulation described above include GABA and glycine.

Another technique used by the SCS system 10 to treat chronic neuropathic pain experienced by the patient in a particular body region will now be described with reference to FIGS. 9-12. This technique treats chronic neuropathic pain through activation of afferent nerve fibers. Simultaneously, inadvertent stimulation of efferent nerve fibers is addressed by raising the activation threshold of those neural structures.

Figure 9:
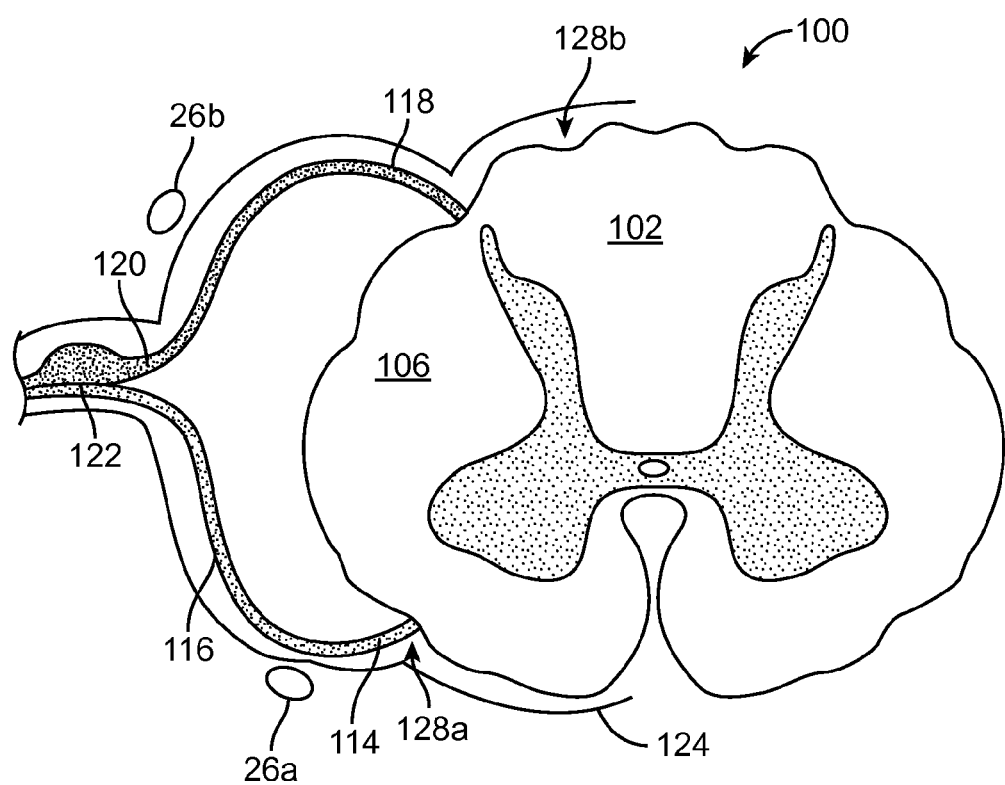
FIG. 9 is a perspective view showing an electrode arrangement relative to the spinal cord and spinal nerves in accordance with a second stimulation regimen of the present invention.

In one example illustrated in FIG. 9, two electrodes 26 may be employed to stimulate an afferent neural structure, such as the dorsal root 118, thereby treating the chronic pain, while inhibiting activation of the ventral root 116, thereby preventing any side-effect that would otherwise result from the inadvertent stimulation of the ventral root 116. To this end, a dorsal electrode 26b is implanted within the dorsal epidural space 128b in a lateralized position located near the dorsal root 118, while a ventral electrode 26a is implanted in the ventral epidural space 128a proximal to the ventral root 116.

Figure 10:
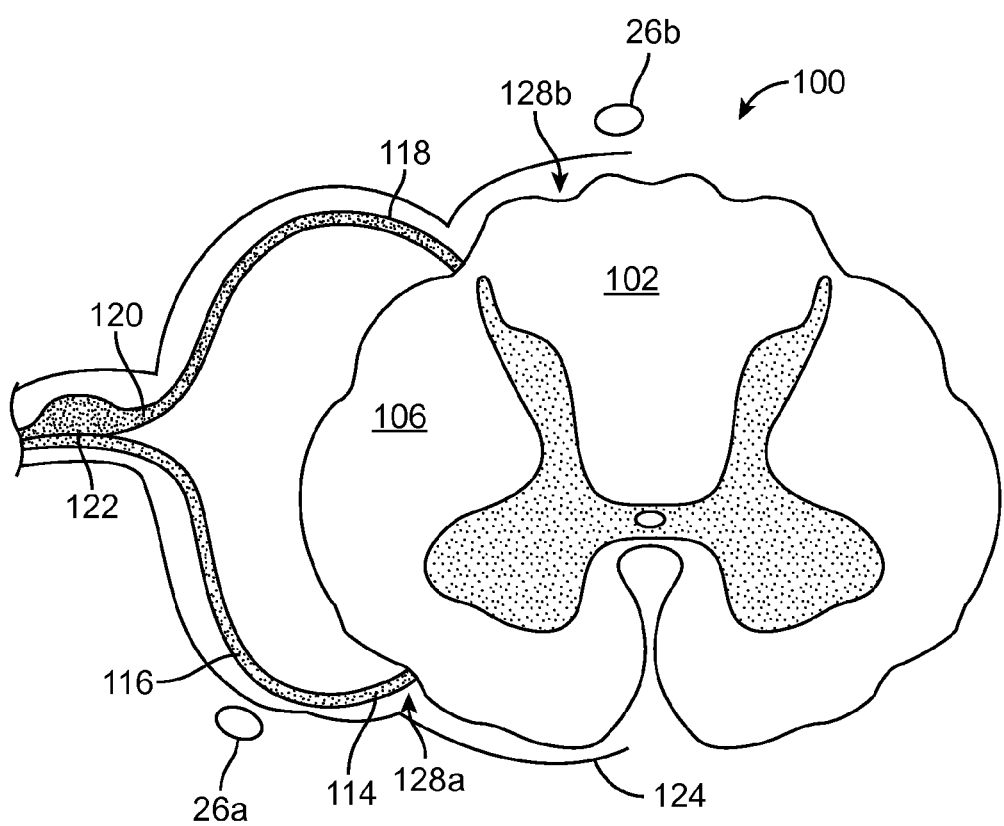
FIG. 10 is a perspective view showing an alternative electrode arrangement relative to the spinal cord and spinal nerves in accordance with a second stimulation regimen of the present invention.

In one example illustrated in FIG. 10, two electrodes 26 may be employed to stimulate an afferent neural structure, such as the dorsal column 102, thereby treating the chronic neuropathic pain, while inhibiting activation of the ventral root 116, thereby preventing any side-effect that would otherwise result from the inadvertent stimulation of the ventral root 116. To this end, a dorsal electrode 26b is implanted within the dorsal epidural space 128b directly above the dorsal column 102, while a ventral electrode 26a is implanted in the manner discussed above with respect to FIG. 9.

Figure 11:
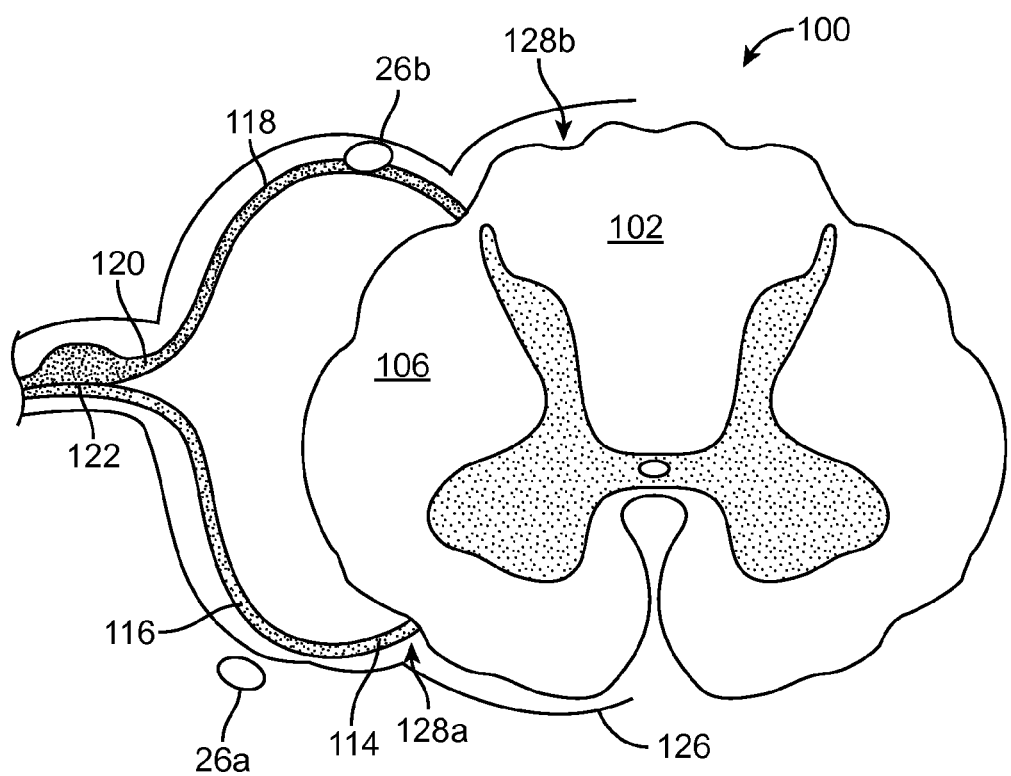
FIG. 11 is a perspective view showing a further electrode arrangement relative to the spinal cord and spinal nerves in accordance with a second stimulation regimen of the present invention.

In still one example illustrated in FIG. 11, two electrodes 26 may be employed to stimulate an afferent neural structure, such as the dorsal portion of the lateral column 106, which carries some nociceptive information via $2^{nd}$ order neurons receiving input from A delta fibers, the activation of which engenders an endogeneous chemical release, thereby treating the chronic pain, while inhibiting activation of the ventral root 116, thereby preventing any side-effect that would otherwise result from the inadvertent stimulation of the ventral root 116. To this end, a dorsal electrode 26b is implanted within the dorsal epidural space 128b near the dorsal portion of the lateral column 106 between a pair of adjacent dorsal roots 118, while a ventral electrode 26a is implanted in the manner discussed above with respect to FIG. 9.

Figure 12:
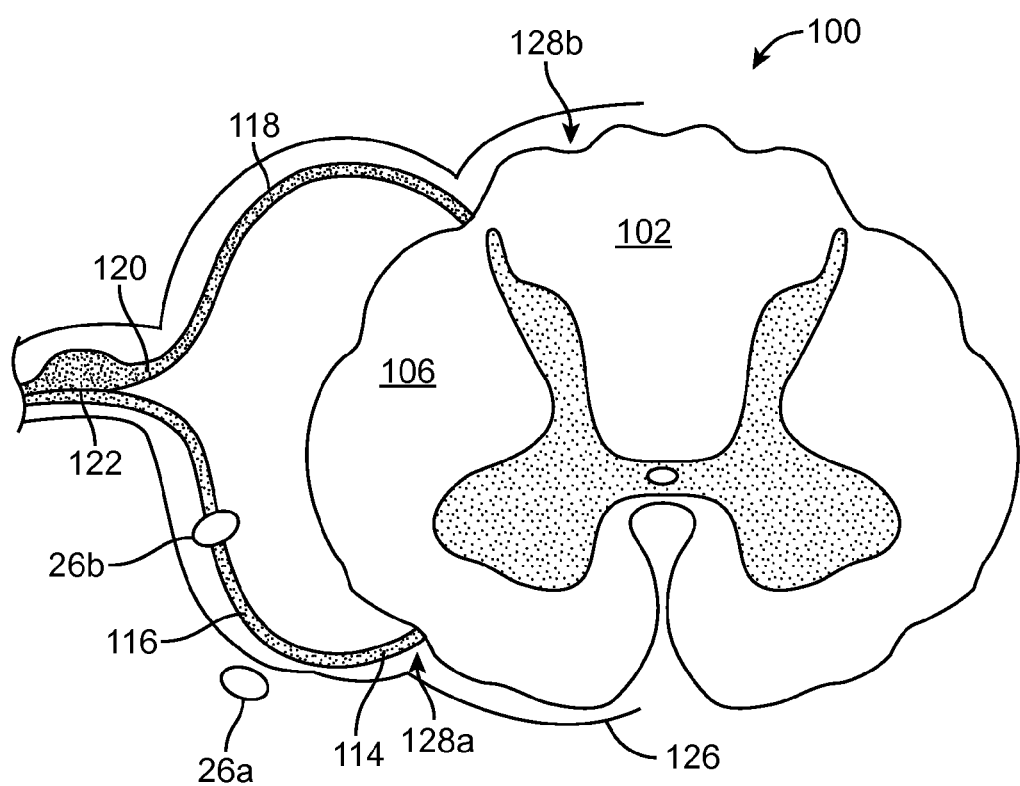
FIG. 12 is a perspective view showing yet another electrode arrangement relative to the spinal cord and spinal nerves in accordance with a second stimulation regimen of the present invention.

In still one example illustrated in FIG. 12, two electrodes 26 may be employed to stimulate an afferent neural structure, such as the ventral portion of the lateral column 106, which carries nociceptive information via $2^{nd}$ order neurons receiving input from A-delta fibers, the activation of which engenders an endogeneous chemical release, thereby treating the chronic pain, while inhibiting activation of the ventral root 116, thereby preventing any side-effect that would otherwise result from the inadvertent stimulation of the ventral root 116. To this end, a dorsal electrode 26b is implanted within the dorsal epidural space 128b near the ventral portion of the lateral column 106 between a pair of adjacent dorsal roots 118, while a ventral electrode 26a is implanted in the manner discussed above with respect to FIG. 9.

The embodiments set out above all illustrate electrodes are implanted on one side of a spinal column 100, and on a single spinal level. Depending on a patient's needs, multiple electrodes can be implanted, occupying sites on both sides of the spinal column and on multiple spinal levels. Although the examples provided above show the afferent neural structures as being the dorsal roots and/or the dorsal and lateral columns of the spinal cord, other afferent neural structures, such as dorso- and ventro-lateral spinal cord tracts, brainstem, cerebellum, peripheral nerves, and/or peripheral field receptors may be stimulated, while inhibiting the neural activity of neighboring efferent neural structures.

Embodiments discussed in connection with FIGS. 9-12 all employ the same general stimulation regime, subject to adaptation for specific patient needs. In these embodiments, the stimulation applied by the dorsal 26b all use typically low-to-medium rate stimulation (1-80 Hz) to stimulate the afferent nerve structures. Electrode combinations, amplitudes, and pulse widths, are determined by the geometry of the specific electrode-to-fiber relationship in a particular therapeutic setting. Those of skill in the art are capable of arriving at appropriate parameter combinations for these values. The ventral electrode 26a, which is positioned identically in all four embodiments, employs a stimulation regimen intended to block transmission or activity in the efferent neural structure, and in this case, the ventral root 116 by applying suppression energy to the VR 116.

The techniques described below apply electrical suppression energy to the efferent neural structure to decrease their activation threshold. Preferably, the ventral and dorsal electrodes 26a, 26b are placed as closely as possible to the neural structures in order to maximize the resolution of the energy transmitted by the electrodes 26a, 26b; that is, to focus the stimulating effect of the stimulation energy on afferent neural structures depending on the particular arrangement (dorsal root 118 (FIG. 9), dorsal column 102 (FIG. 10), dorsal portion of the lateral column 106 (FIG. 11), or the anterior portion of lateral column 106 (FIG. 12)), and to focus the activation-threshold-increasing effect of the suppression energy on the efferent neural structure (in the illustrated cases, the ventral root 116). Preferably, the proximity of the electrodes 26a, 26b to the neural structures should be less than resolution few millimeters to ensure focused neuromodulation on the intended structure. Because the electrodes 26a, 26b are typically separated from the neural structures by the dura mater 124 and spinal cord fluid, there will typically be some distance between the electrodes 26a, 26b and the neural structures, with the distance varying from patient to patient. If implanted within the cervical region of the spine, the distance from the electrodes 26a, 26b to the neural structures will typically be quite small, and therefore, high focus can be achieved. If implanted within the thoracic region of the spine, the distance from the electrodes 26a, 26b to the neural structures will be greater, and therefore, it will be more difficult to focus the neuromodulation energy on the intended target. In all cases, the addition of more electrodes spaced close together on the leads 12 will improve the ability to focus the neuromodulation energy.

In one technique for preventing inadvertent stimulation of the efferent neural structure, the electrodes 26a, 26b are configured as a bipole, such that the ventral electrode 26a adjacent the efferent neural structure is an anode, and the dorsal electrode 26b adjacent the afferent neural structure is a cathode. In this configuration, electrical stimulation energy conveyed between the cathode and anode creates an electrical field that stimulates the afferent neural structure, while preventing stimulation of the efferent neural structure. That is, the electrical current sourced by the ventral electrode 26a hyperpolarizes the efferent neural structure, thereby increasing its activation threshold, while the electrical current sunk by the dorsal electrode 26b depolarizes the afferent neural structure, thereby creating a locus of stimulation that is confined to the afferent neural structure adjacent the dorsal electrode 26b. In effect, the dorsal electrode 26b generates the electrical stimulation energy at the afferent neural structure, while the ventral electrode 26a "pushes" the electrical stimulation energy away from the efferent neural structure.

It is desirable that the locus of stimulation be as focal as possible without increasing its reach, thereby stimulating the afferent neural structure, while preventing stimulation of the efferent neural structure. In the case where the dorsal electrode 26b is far from the afferent neural structure, an increase in sunk current would be required. This would require an increase in the electrical current sourced at the ventral electrode 26a. However, this might result in inadvertent activation of the efferent neural structure, due to the nature of the depolarizing sidelobes of the activating function along the efferent neuron, which may lead to undesirable outcomes (e.g., discomfort or undesirable reflexive activity). As such, a portion of the electrical current sourced at the ventral electrode 26a can be additionally sunk at a remote electrode (e.g., the case or even a therapeutic electrode remote from the bipole configuration), thereby creating a local current imbalance at the target site of the afferent neural structure.

Further details discussing the use of bipolar electrode arrangements to render tissue less excitable to inadvertent stimulation are disclosed in U.S. patent application Ser. No. 11/300,963, entitled "Apparatus and Methods for Stimulating Tissue," which is expressly incorporated herein by reference.

In another technique for preventing inadvertent stimulation of the efferent neural structure, a sub-threshold, disabling conditioning pre-pulse can be applied by the ventral electrode 26a to the adjacent efferent neural structure, and a depolarizing stimulation pulse can be subsequently applied by the dorsal electrode 26b to the afferent neural structure involved in a particular embodiment, which could be the DC fibers, the DR fibers, and structures which receive input from afferent neurons, such as the dorsolateral ascending fibers, or the ventrolateral ascending fibers. The duration between the conditioning pulse and the stimulation pulse is preferably zero, but at the least should be less than 100 µs, and more preferably, less than 30 µs. The conditioning pre-pulse preferably has a duration dependent upon the polarity of the disabling pre-pulse. In the case of a hyperpolarizing pre-pulse, the duration is relatively short, preferably less than 200 µs, more preferably less than 150 µs, and most preferably less than 75 µs, such that m-gates of the sodium ion channels in the neural axons are closed to render the tissue less excitable to subsequent stimulation. The subsequent stimulation pulse preferably has a relatively short duration, e.g., less than 200 µs. Alternatively, in the case of a depolarizing pre-pulse, the pulse duration is relatively long, preferably greater than 500 µs, and is applied by the ventral electrode 26a, such that h-gates of the sodium ion channels in the neural axons are closed to render the tissue even less excitable to subsequent stimulation.

Further details discussing the use of conditioning pre-pulses to render tissue less excitable to subsequent stimulation are disclosed in U.S. patent application Ser. No. 11/752,895, entitled "Short Duration Pre-Pulsing to Reduce Stimulation-Evoked Side-Effects," which is expressly incorporated herein by reference.

In still another technique for preventing inadvertent stimulation of the efferent neural structure, electrical background energy is conveyed from the ventral electrode 26a in accordance with at least one stochastic parameter. If the electrical background energy is in the form of pulses, the stochastic parameter may comprise at least one of an interpulse interval, pulse amplitude, pulse shape, and pulse duration. If the electrical background energy is white noise, the stochastic parameter may be a frequency.

The ventral and dorsal electrodes 26a, 26b can be configured as stimulating electrodes in a bipolar arrangement (the dorsal electrode 26b as the cathode, and the ventral electrode 26a as the anode) in a manner described above, while the ventral electrode 26a can be configured as a background electrode in a monopolar arrangement with the IPG case 44. Thus, electrical stimulation energy is conveyed between the bipolar arrangement of the electrodes 26a, 26b, thereby therapeutically stimulating the afferent neural structure, and electrical background energy is conveyed between the ventral electrode 26a and the IPG case 44, thereby decreasing the excitability of the efferent neural structure.

Notably, due to the monopolar arrangement, the field strength of the electrical background energy conveyed from the ventral electrode 26a decays at a relatively low rate with distance. As such, the ventral electrode 26a may be relatively far from the efferent neural structure for it to modulate the excitability of the efferent neural structure. Alternatively, the electrical background energy may be conveyed from ventral electrode 26a in a bipolar arrangement. However, in this case, due to current shunting, the ventral electrode 26a must be relatively close to the efferent neural structure. In either case, as a general rule, the excitability of the efferent neural structure will be decreased if the magnitude of the electrical background energy is relatively high.

Because the excitability of the efferent neural structure will be decreased by the electrical background energy, the effect of any inadvertent conveyance of electrical stimulation energy to the efferent neural structure will be decreased. In one method, the electrical background energy is set equal to or higher than 10% of the perception threshold of the patient. Preferably, the electrical background energy is sub-threshold (i.e., does not stimulate nerve fibers), but may be supra-threshold if it provides therapy to the patient or can otherwise be tolerated by the patient. Ultimately, the magnitudes of the electrical stimulation energy and electrical background energy can be set relative to each other through trial and error.

Further details discussing the use of electrical background energy to render tissue less excitable to subsequent stimulation are disclosed in U.S. patent application Ser. No. 12/501,127, entitled "System and Method for Reducing Excitability of Dorsal Root Fiber by Introducing Stochastic Background Noise," which is expressly incorporated herein by reference.

In yet another technique for preventing inadvertent stimulation of the efferent neural structure, which works particularly well if the efferent neural structure extends over the targeted afferent neural structure (e.g., if the dorsal root 118 is to be stimulated, the ventral root 116 may be interposed between a stimulating electrode located in the ventral epidural space 128a and the dorsal root 118, and is therefore closer to the stimulating electrode than the afferent neural structure, the electrical stimulation energy takes the form of high frequency (e.g., in the range of 2-30 KHz) time-varying electrical energy (e.g., a sinusoidal energy), the frequency and amplitude of which may be selected to increase the activation threshold of the relatively close neural structure, while stimulating the relatively far neural structure.

This ability is due, in large part, because the blocking threshold of a nerve fiber by high frequency electrical energy is higher than the threshold at which the nerve fiber is activated by the same high frequency electrical energy. Thus, if the high frequency electrical energy has an amplitude that is higher than the blocking threshold of relatively close nerve fibers, the relatively far nerve fibers at a particular depth will still have a blocking threshold above the amplitude of the high frequency electrical energy, but a stimulation threshold below the amplitude of the high frequency electrical energy. This means that relatively close nerve fibers will be blocked at a stimulation current that activates relatively far nerve fibers.

The desired depth range of blocked nerve fibers and the desired depth range of the stimulated nerve fibers may be tuned by selecting the amplitude and frequency of the high frequency electrical energy. In general, as the amplitude of the high frequency electrical energy is increased, the range of distance in which neural structures are blocked increases, and the range of distance in which the neural structures are stimulated decreases.

Further details discussing the use of high frequency electrical energy to block action potentials in closer neural tissue while stimulating further neural tissue are disclosed in U.S. patent application Ser. No. 12/819,107, entitled "Spatially Selective Nerve Stimulation in High-Frequency Nerve Conduction Block and Recruitment," which is expressly incorporated herein by reference.

In an optional embodiment, a set of sensors, such as sense amplifiers, accelerometers, chemical sensors, or thermal sensors, may be employed to ensure that the stimulation applied is efficacious, as well as to identify side effects arising from stimulation activity. For example, the SCS system 10 can use device triggering and/or sensing of the activity of the afferent response and/or efferent response to determine when suppression energy is to be delivered. For example, if the dorsal root 118 is stimulated and a sensory action potential is generated and detected by the sensors, this can provide a trigger that starts a window in which undesired orthodromic neural activity is looked for. When such orthodromic neural activity is sensed by the sensors, the SCS system 10 may initiate the suppression technique intended to inhibit the undesired neural activity. Alternatively, the suppression technique used to inhibit activity in the efferent neural structure can simply be initiated upon delivery of the stimulation energy to the afferent structure.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient suffering from a medical ailment using at least one electrode adjacent an efferent neural structure and at least another electrode adjacent an afferent neural structure, the method comprising:
    applying electrical stimulation energy by the at least one electrode to the efferent neural structure, thereby increasing the activation threshold of the efferent neural structure relative the afferent neural structure; and
    applying electrical stimulation energy by the at least other electrode to the afferent neural structure while the activation threshold of the efferent neural structure is increased, thereby modulating activity of the afferent neural structure to treat the medical ailment, wherein the increasing of the activation threshold of the efferent neural structure minimizes any stimulation of the efferent neural structure inadvertently caused by the electrical stimulation energy applied by the at least one other electrode to the efferent neural structure.

2. The method of claim 1, wherein the medical ailment is chronic pain.

3. The method of claim 1, wherein stimulation of the efferent neural structure that would otherwise occur absent the increased activation threshold is prevented.

4. The method of claim 1, wherein the electrical stimulation energy is epidurally applied to the afferent neural structure and the efferent neural structure.

5. The method of claim 1, wherein the efferent neural structure is a ventral root fiber.

6. The method of claim 5, wherein the afferent neural structure is a dorsal root fiber.

7. The method of claim 5, wherein the afferent neural structure is one of a dorso-spinal column fiber, dorso-lateral spinal column fiber, and a ventro-lateral spinal column fiber.

8. The method of claim 1, wherein the activation threshold of the efferent neural structure relative to the activation threshold of the afferent neural structure is increased by applying electrical suppression energy by the at least one electrode to the efferent neural structure.

9. The method of claim 8, wherein the electrical stimulation energy is applied to the afferent neural structure by sinking electrical current into the at least one other electrode adjacent the afferent neural structure, thereby treating the medical ailment, and the electrical suppression energy is applied to the efferent neural structure by sourcing at least a portion of the electrical current from the at least one electrode adjacent the efferent neural structure, thereby increasing the activation threshold of the efferent neural structure.

10. The method of claim 8, further comprising sinking at least a portion of the electrical current sourced at the at least one electrode into a remote electrode.

11. The method of claim 8, wherein the activation threshold of the efferent neural structure is increased by applying a sub-threshold, disabling conditioning pre-pulse by the at least one electrode to the efferent neural structure, and electrical stimulation energy is applied by the at least one other electrode to the afferent neural structure by applying a depolarizing stimulation pulse to the afferent neural structure.

12. The method of claim 11, wherein the conditioning pre-pulse is a hyperpolarizing pulse having a duration less than 200 μs.

13. The method of claim 1, wherein the activation threshold of the efferent neural structure is increased by applying electrical background energy by the at least one electrode to the efferent neural structure in accordance with at least one stochastic parameter.

14. The method of claim 13, wherein the electrical background energy comprises pulses, and the at least one stochastic parameter comprises at least one of an interpulse interval, pulse amplitude, pulse shape, and pulse duration.

15. The method of claim 13, wherein the electrical background energy comprises white noise, and the at least one stochastic parameter comprises a frequency.

16. The method of claim 1, further comprising sensing neural activity in the efferent neural structure in response to the application of electrical stimulation energy to the afferent neural structure by the at least other electrode, wherein the electrical stimulation energy is applied to the efferent neural structure by the at least one electrode in response to sensing of the neural activity in the efferent neural structure.

* * * * *